United States Patent [19]

Brown et al.

[11] Patent Number: 5,677,481
[45] Date of Patent: Oct. 14, 1997

[54] VISCOSITY MAINTENANCE

[75] Inventors: Robert G. Brown, Keene, N.H.; Arne Johannessen, Greenfield, Mass.

[73] Assignee: Markem Corporation, Keene, N.H.

[21] Appl. No.: 614,162

[22] Filed: Mar. 8, 1996

[51] Int. Cl.[6] .......................... G01N 11/14; G01N 11/00; G05D 11/00; B41J 29/38
[52] U.S. Cl. .......................... 73/54.28; 73/54.01; 137/92; 347/17
[58] Field of Search .......................... 73/54.31, 54.28, 73/54.29, 54.33, 54.34, 54.01, 54.14, 54.18, 54.23, 54.26, 54.32, 54.35; 101/150, 153, DIG. 45; 137/92; 347/17

[56] References Cited

U.S. PATENT DOCUMENTS

| | | | |
|---|---|---|---|
| 3,677,070 | 7/1972 | Norcross | 73/57 |
| 4,499,753 | 2/1985 | Carr | 73/59 |
| 4,668,911 | 5/1987 | Mueller et al. | 324/208 |
| 4,878,378 | 11/1989 | Harada | 73/59 |
| 5,131,265 | 7/1992 | Tobin et al. | 73/54.23 |

OTHER PUBLICATIONS

Knopf, M., "Use Torque Sensors in Small Mixers to Measure Viscosity," *Today's Chemist At Work*, Dec., 1994.

*Primary Examiner*—Hezron E. Williams
*Assistant Examiner*—Jay L. Politzer
*Attorney, Agent, or Firm*—Fish & Richardson, P.C.

[57] ABSTRACT

A device for measuring relative viscosity includes a fluid reservoir, a stirrer, and a sensing system. The stirrer has two members, with one member being more bendable than the other. When the stirrer is moving, the sensing system detects a differential bend between the members; the differential bend is related to the viscosity of a fluid in the fluid reservoir. The sensing system includes two spaced sensors which detect when magnets on the members pass the sensors. A timer provides a time lapsed between passage of one of the members past a sensor and passage of the other member past the other sensor. The time lapsed is related to the viscosity of the fluid in the fluid reservoir. A controller automatically controls the addition of a solvent to the fluid within the fluid reservoir; the addition of the solvent is dependent on the time lapsed.

24 Claims, 5 Drawing Sheets

VISCOSITY MAINTENANCE

BACKGROUND OF THE INVENTION

The invention relates to measuring viscosity.

The desired viscosity of the ink in a gravure printing machine is a function of the substrate, the speed of printing, and the ink type. The viscosity of the ink is effected by solvent evaporation and the temperature of the environment.

SUMMARY OF THE INVENTION

In general, in one aspect, the invention features a device for measuring relative viscosity. The device includes a fluid reservoir, a stirrer movably mounted within the fluid reservoir, and a sensing system. The stirrer has two members, with one member being more bendable than the other, for example, one arm is rigid and one arm is flexible. When the stirrer is moving, a sensing system detects a differential bend between the members, the differential bend is related to the viscosity of a fluid in the fluid reservoir.

Implementations of the invention may include one or more of the following features. The stirrer rotates. The members are arms each with a magnet located at the end of the arm. The arms extend from a center of rotation of the stirrer. The sensing system is a sensor which detects when the magnets pass the sensor. There are two spaced sensors which detect when the magnets pass the sensors. A timer provides a time lapsed between passage of one of the members past a sensor and passage of the other member past the other sensor. The time lapsed is related to the viscosity of the fluid in the fluid reservoir. A magnet-coupling drive moves the stirrer. A controller automatically controls the addition of a solvent within a solvent reservoir to a fluid within the fluid reservoir. The addition of the solvent is dependent on the time lapsed which is related to the viscosity of the fluid. A conduit leads from the solvent reservoir to the fluid reservoir. A flow controller, e.g., a pump or solenoid, controls flow through the conduit.

In general, in another aspect, the invention features a printing machine including an ink reservoir, a gravure roll, a stuffer roll for transferring ink from the ink reservoir to the gravure roll, and a device for measuring relative viscosity located in the ink reservoir.

Implementations of this aspect of the invention may include one or more of the following features. The ink reservoir is mounted for easy removal and cleaning.

In general, in another aspect, the invention features a method of measuring relative viscosity. The method includes placing a fluid in a fluid reservoir; moving a stirrer mounted within the fluid reservoir, the stirrer including two members, one of which is more bendable than the other; and detecting a differential bend between the members when the stirrer moves, the differential bend being related to the viscosity of a fluid in the fluid reservoir.

Implementations of this aspect of the invention may include one or more of the following features. The detection of the differential bend includes timing the time lapsed between passage of one of the members past a sensor and passage of the other of the members past a sensor. The time lapsed is related to the viscosity of a fluid in the fluid reservoir.

In general, in another aspect, the invention features a method of maintaining viscosity. The method includes automatically controlling the addition of a solvent from a solvent reservoir to the fluid within the fluid reservoir.

Advantages of the invention may include one or more of the following.

The viscosity measuring device is located in the ink reservoir itself and thus measures the viscosity of the ink near the transfer point of the ink from the gravure roll to the printing roll. This provides consistent, high quality printed images.

The viscosity of the ink is continuously maintained by the automatic addition of solvent.

Other advantages and features will become apparent from the following description and from the claims.

DESCRIPTION OF THE PREFERRED EMBODIMENTS

Figure 1:
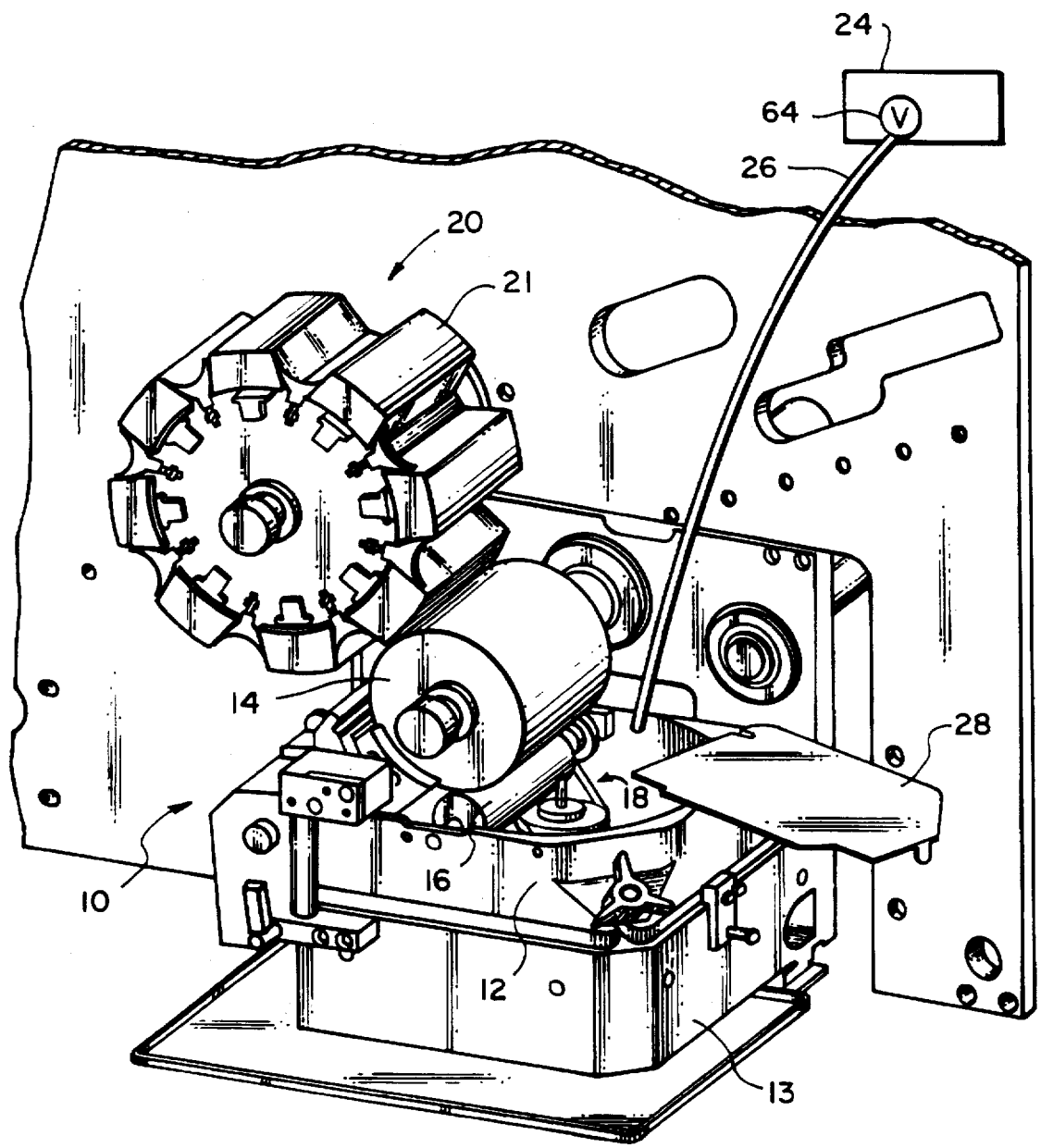
FIG. 1 is a diagrammatic representation of a gravure printing machine with a viscosity maintenance device.

Referring to FIG. 1, a rotary gravure printing machine 10 includes an ink reservoir 12 supported by a base 13, a gravure roll 14, a stuffer roll 16 for transferring ink from ink reservoir 12 to gravure roll 14, and a relative viscosity measuring device 18 located in ink reservoir 12. A printing roll 20 having elastomeric pads 21 picks up the inked image from the etched cells (not shown) of gravure roll 14 for printing on a substrate (not shown). The viscosity of the ink located in ink reservoir 12 is adjusted by the addition of a solvent. A solvent reservoir 24 and conduit 26 are provided for adding the solvent. Solvent reservoir 24 includes a flow controller 64, e.g., a pump or solenoid, for controlling the flow of solvent in conduit 26. A cover 28, shown here in its open position, may be included to prevent spillage of the ink from ink reservoir 12, to minimize solvent evaporation from the reservoir, and to keep foreign debris out of the reservoir.

Figure 2:
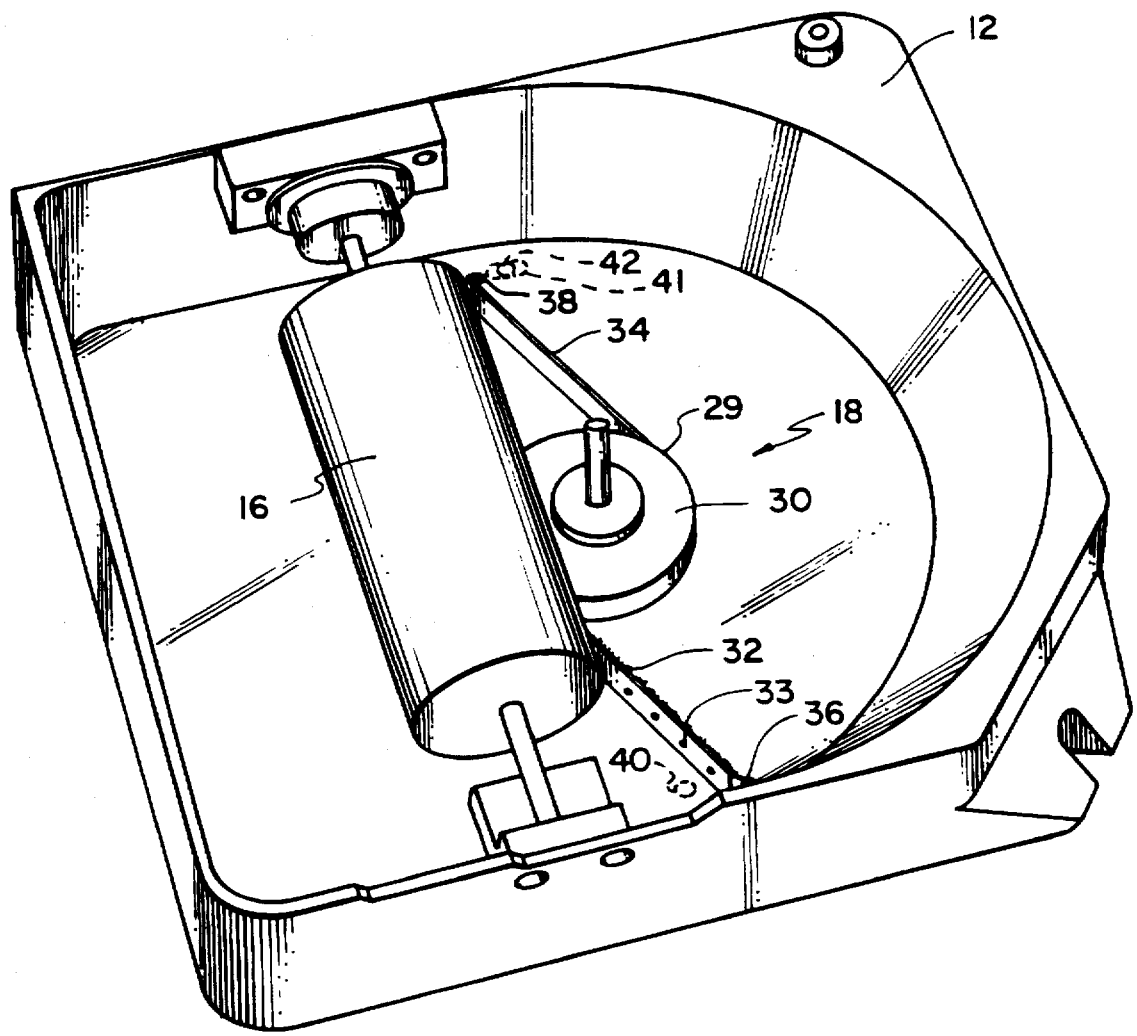
FIG. 2 is a perspective view of the ink reservoir including a viscosity measuring device.
Figure 2A:
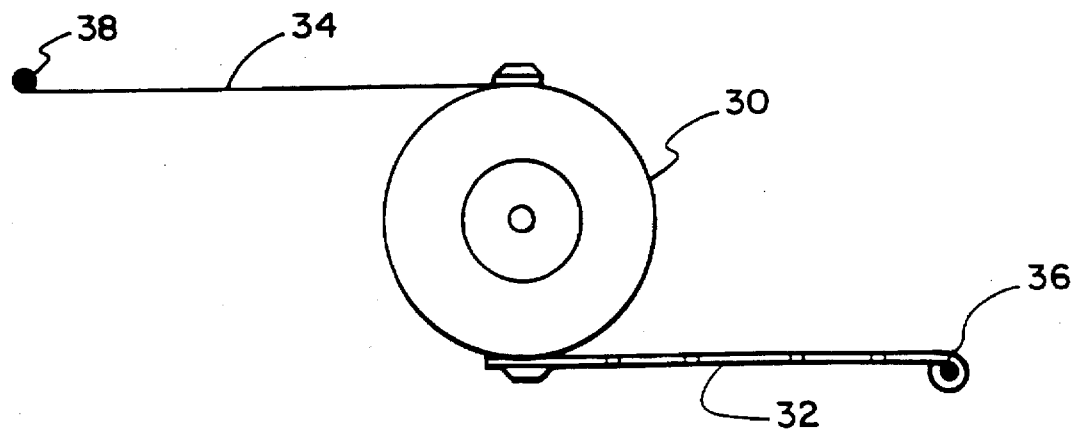
FIG. 2A is a top view of a stirrer of the viscosity measuring device.

Referring to FIGS. 2–2A, a rotating stirrer 29 located in ink reservoir 12 serves the dual function of mixing the ink and measuring viscosity when rotated. Stirrer 29 includes a coupling assembly 30, a rigid paddle 32, and a flexible paddle 34. The paddles help mix the ink by agitation and rigid paddle 32 includes holes 33 which aid in mixing by creating a shearing action rather than a wave as the paddle goes through the ink. Stuffer roll 16 also helps mix the ink, being particularly useful in mixing solvent with the ink.

Paddles 32, 34 include magnets 36, 38, respectively, located at the ends of the paddles and spaced 180° apart. Flexible paddle 34 is about ⅜" longer than rigid paddle 32 resulting in a ⅜" offset between the magnet locations. Sensors 40, 42 of viscosity measuring device 18, for example, OMNI-POLAR hall effect sensors from MICROSWITCH Freeport, Ill, part #SR4P2-A1, having a sensitivity range down to about seven gauss and wired in parallel, are adjustably spaced about 160° apart, mounted with a ⅜" offset, and located a distance of about ⅛–¼" from magnets 36, 38 when the magnets are positioned over the sensors. A signal is transmitted by sensors 40, 42 when a magnet crosses over the sensor. Though shown in FIG. 2 for clarity, sensors 40, 42 are preferably mounted in base 13.

Sensor 42, or alternatively sensor 40 or both sensors, is adjustably mounted in a slot 41. The position of sensor 40 is set such that the time delay between the crossing, e.g., of rigid paddle 32 over sensor 40, is 50 ms ahead of the crossing, e.g., of flexible paddle 34 over sensor 42, when stirrer 29 is rotated clockwise in a dry reservoir.

Rotation of stirrer 29 within a volume of ink causes paddle 34 to bend while paddle 32 remains rigid. The amount of bend of flexible paddle 34 is indicative of the viscosity of the ink. The time delay between the crossing of rigid paddle 32 over one of the sensors and the crossing of flexible paddle 34 over the other sensor, for example, for clockwise rotation, the crossing of rigid paddle 32 over sensor 40 and the subsequent crossing of flexible paddle 34 over sensor 42, gives a measure of the relative viscosity of the ink; the greater the time delay the higher the viscosity.

Rigid paddle 32 is made from, e.g., stainless steel, and flexible paddle 34 is made from a more flexible material, e.g., spring steel. The thickness of flexible paddle 34 is dependant upon the expected viscosity range of the ink, e.g., 1–3,000 centipoise the thickness is 0.005", 3,000–5,000 centipoise the thickness is 0.007", and >5,000 centipoise the thickness is 0.01". The thickness of rigid paddle 32, e.g., 0.06", is selected to prevent any bending of the paddle in all viscosities that will be encountered in use of the device. The paddles generally have heights of about ⅜" with rigid paddle 32 having a length of about 2 ⅝" and flexible paddle 34 having a length of about 3". Magnets 36, 38, e.g., samarium-cobalt magnets with nickel plating for chemical resistance, having about ⅛" diameter and ¼" length, are mounted with their north poles facing toward sensors 40, 42. The magnets are selected to be powerful enough to be detected through reservoir 12 while small enough to provide good sensitivity and accuracy.

Figure 2B:
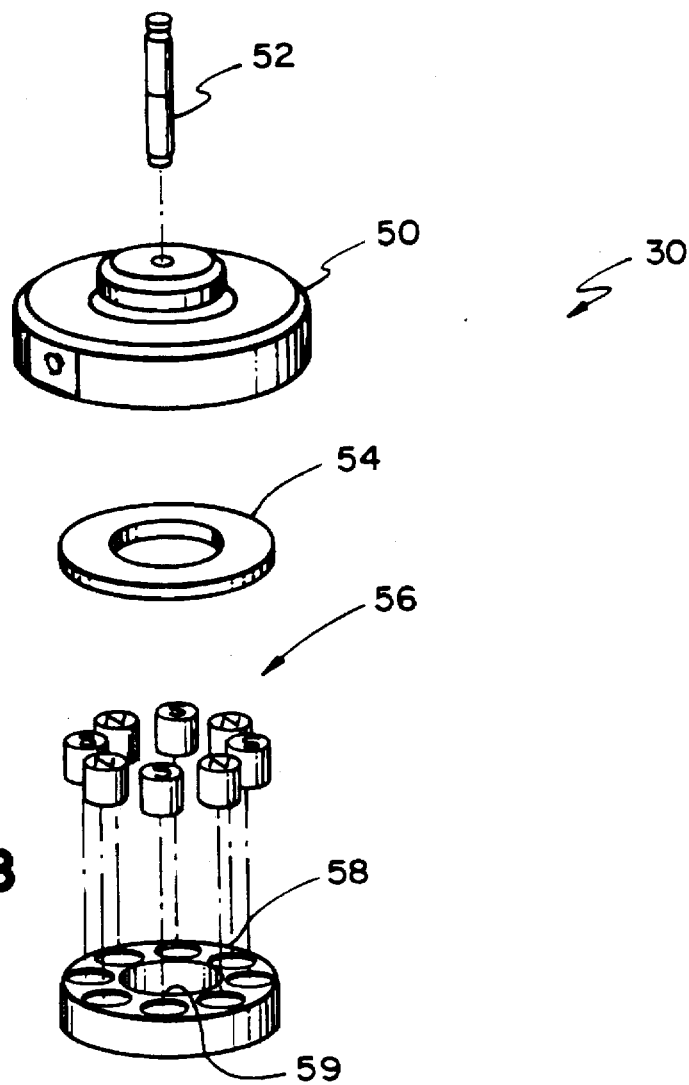
FIG. 2B is an exploded view of a coupling assembly of the stirrer.

Referring to FIG. 2B, coupling assembly 30 includes a stirrer housing 50, made from, e.g., DELRIN®, a grooved pin 52, a washer 54, samarium cobalt magnets 56 and a magnet holder 58. A magnet drive, such as taught in U.S. Pat. No. 3,677,070 to Norcross, incorporating a motor 62 (see FIG. 3), e.g., a stepper motor running at 18 rpm, can be used to drive coupling assembly 30. Magnetic coupling allows ink reservoir 12 to be easily removed from machine 10 for cleaning. Ink reservoir 12 is made from a chemical resistant, non-magnetic material that does not interfere with the magnetic coupling, e.g., preferably aluminum, though DELRIN, polypropylene, stainless steel, or a ceramic can be used. Ink reservoir 12 includes a raised projection (not shown) over which a bore 59 of magnet holder 58 is placed to position coupling assembly 30 in the reservoir. Stirrer 29 can be easily removed from reservoir 12 for cleaning by lifting up on pin 52.

Figure 3:
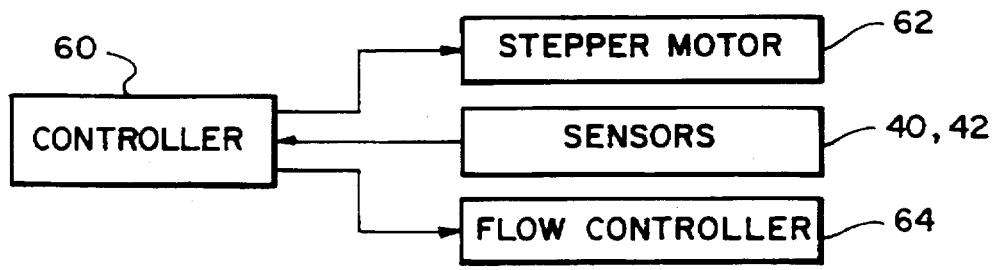
FIG. 3 is a block diagram of the control system.

Referring to FIG. 3, a controller 60 controls stepper motor 62 to rotate stirrer 29. Sensors 40, 42 transmit a signal to controller 60 at each crossing of the magnets over the sensors. Controller 60 measures the time delay between the magnet crossings and compares this time delay to a predetermined desired time delay range. The predetermined desired time delay range is related to the desired viscosity range of the ink. Though the absolute viscosity of the ink could be determined by the time delay, only knowledge of the relative viscosity as measured by the time delay is needed to adjust the viscosity. If the time delay is too long, i.e., the viscosity is high, controller 60 relays a signal to flow controller 64 to allow flow of solvent through conduit 26 to ink reservoir 12.

The solvent addition parameters, i.e., the number of solvent squirts per solvent addition, for example three squirts, the volume of solvent delivered in each squirt, for example, 0.102 ml using MARKEM ZY thinner which corresponds to a 200 ms delivery, the time between each solvent squirt in a solvent addition, for example, four seconds, and the time delay between the end of a solvent addition and the next allowed solvent addition, for example, 40 seconds, may be pre-programmed into controller 60 for each solvent or operator setable.

Figure 4:
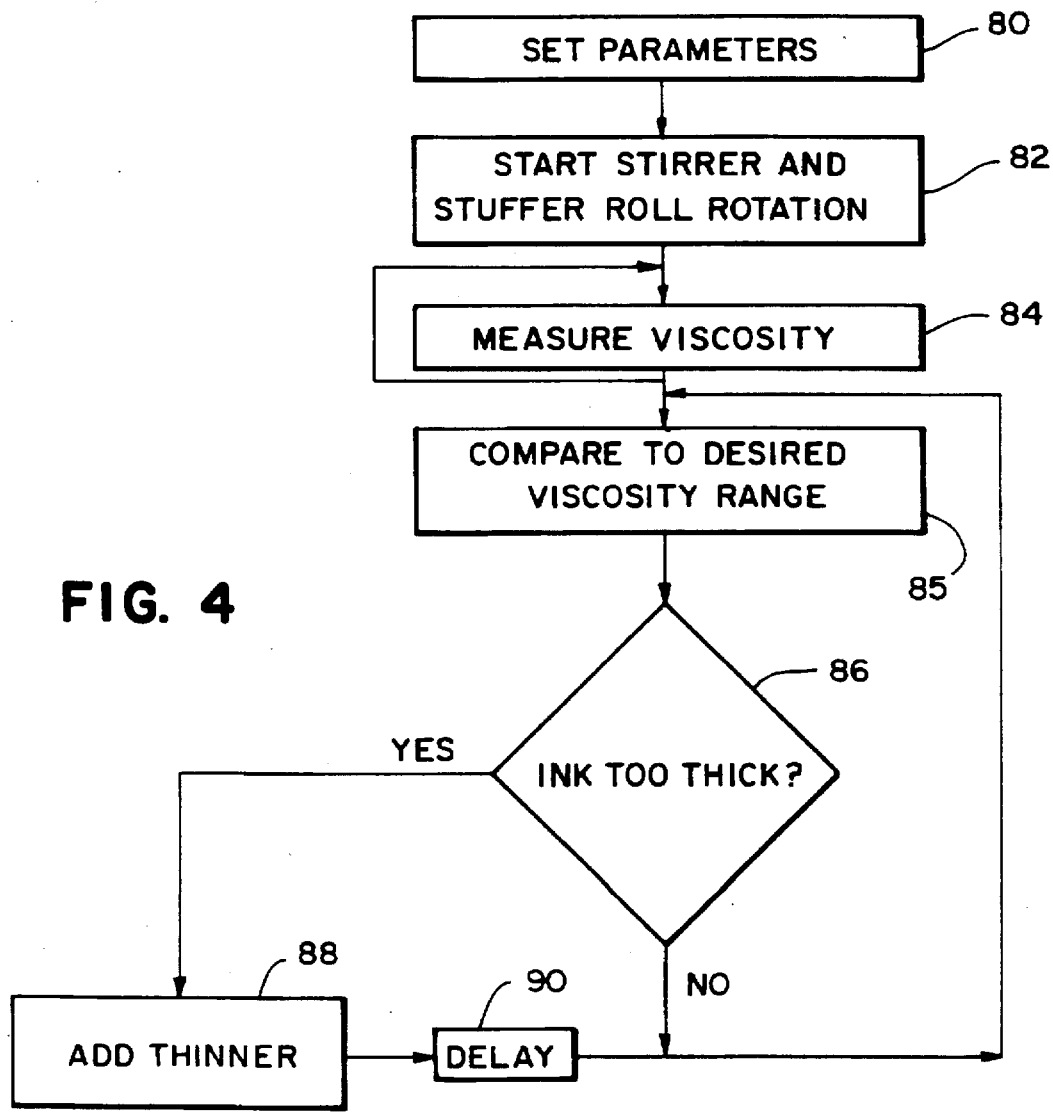
FIG. 4 is a block diagram of the control algorithm of the viscosity maintenance device.
Figure 5:
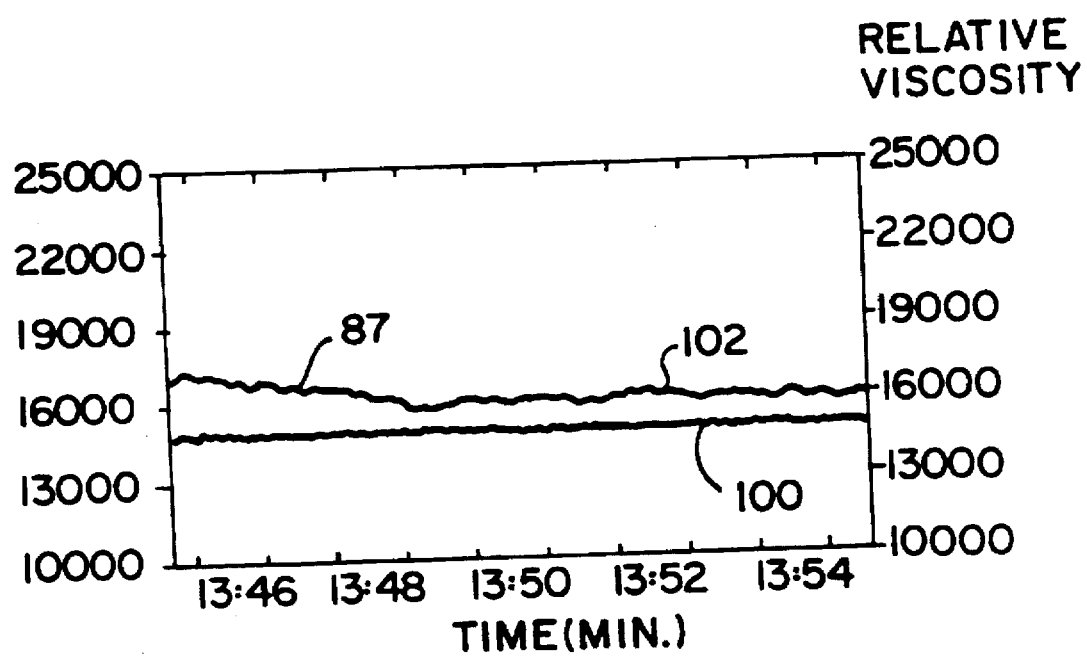
FIG. 5 shows a display of the relative viscosity of the ink under control of the viscosity maintenance device.

Referring to FIGS. 4 and 5, in use, the operator, at step 80, sets the desired operating parameters including the desired relative viscosity 100, an acceptable relative viscosity range 102 in which the ink has the required properties for printing, and the particular solvent being used. The operator then starts the rotation of the stirrer and stuffer roll to mix the ink at 82. Stirrer 29 rotates, for example, at 18¼ rpm. The viscosity is measured at 84, for example, once per revolution of the stirrer for a measurement at about every three seconds, and compared to the desired viscosity range at 85. Alternatively, the viscosity can be measured twice per revolution if the magnets and sensors are not mounted with an offset. If the measured viscosity 87 (FIG. 5) is above the desired viscosity range, i.e., the ink is too thick, at 86, solvent is added at 88. After the set number of squirts are added to the ink, there is a time delay at 90 before the next solvent addition is made. During this time delay, the additional solvent is mixed into the ink by the action of the stirrer and stuffer roll.

FIG. 5 shows a typical output of the measured relative viscosity 87 compared to the desired relative viscosity 100 and the acceptable range 102 during the addition of solvent to the lower the viscosity of the ink.

In an alternative scheme, automatic control of solvent addition can be eliminated and controller 60 can provide a signal to the operator indicating that the viscosity of the ink is high and the operator can add solvent by hand.

Other embodiments are within the scope of the following claims.

The spacing of magnets 36, 38 and sensors 40, 42 can be other than 180° apart. One sensor instead of two sensors can be used. The principle is in essence the same as the two sensor system, though here one sensor detects when each paddle crosses the sensor position with the time delay again being related to viscosity.

What is claimed is:

1. A device for measuring relative viscosity, comprising:
   a fluid reservoir,
   a stirrer movably mounted within said fluid reservoir, said stirrer including two members, one of said members being more bendable than the other of said members, and
   a sensing system that detects a differential bend between said members when said stirrer moves, said differential bend being related to a viscosity of a fluid when the fluid is included in said fluid reservoir.

2. The device of claim 1 wherein said stirrer rotates.

3. The device of claim 1 wherein each member includes a magnet.

4. The device of claim 3 wherein each member comprises an arm, said magnet being located at an end of said arm.

5. The device of claim 3 wherein said sensing system comprises a sensor, said sensor detects when said magnets pass said sensor.

6. The device of claim 5 wherein said sensing system comprises two spaced sensors, said sensors detect when said magnets pass said sensors.

7. The device of claim 6 further including a timer that provides a time lapsed between passage of one of said members past one of said sensors and passage of the other of said members past the other of said sensors, said time lapsed being related to the viscosity of the fluid when the fluid is included in said fluid reservoir.

8. The device of claim 1 further including a magnet-coupling drive to move said stirrer.

9. The device of claim 1 wherein one of said members is rigid and one of said members is flexible.

10. The device of claim 1 further including a solvent reservoir, and a controller for controlling addition of a solvent within said solvent reservoir to a fluid within said fluid reservoir.

11. The device of claim 10 wherein said controller automatically controls the addition of solvent, addition of said solvent being dependent on said time lapsed.

12. A device for measuring relative viscosity, comprising:

a fluid reservoir, a stirrer rotatably mounted within said fluid reservoir, said stirrer having first and second arms extending from a center of rotation of said stirrer, one of said arms being more bendable than the other of said arms, each arm including a magnet mounted at an end of said arm, two sensors mounted in said device for detecting when said magnets pass said sensors when said stirrer rotates, a timer that provides the time lapsed between passage of one of said members past one of said sensors and passage of the other of said members past the other of said sensors, said time lapsed being related to a viscosity of a fluid when the fluid is included in said fluid reservoir.

13. A viscosity maintenance device, comprising:

a fluid reservoir, a stirrer movably mounted within said fluid reservoir, said stirrer including two members, one of said members being more bendable than the other of said members, a sensing system that detects a differential bend between said members when said stirrer moves, said differential bend being related to a viscosity of a fluid when the fluid is included in said fluid reservoir a solvent reservoir, and a controller for controlling addition of a solvent within said solvent reservoir to a fluid within said fluid reservoir.

14. The device of claim 13 wherein each member includes a magnet.

15. The device of claim 14 wherein said sensing system comprises two spaced sensors, said sensors detect when said magnets pass said sensors.

16. The device of claim 15 further including a timer that provides a time lapsed between passage of one of said members past a sensor and passage of the other of said members past the other of said sensors, said time lapsed being related to the viscosity of the fluid when the fluid is included in said fluid reservoir.

17. The device of claim 16 wherein said controller automatically controls the addition of solvent, addition of said solvent being dependent on said time lapsed.

18. The viscosity maintenance device of claim 13 further including a conduit leading from said solvent reservoir to said fluid reservoir.

19. The viscosity maintenance device of claim 18 further including a flow controller for controlling flow of solvent in said conduit.

20. A method of measuring relative viscosity, comprising:

placing a fluid in a fluid reservoir, moving a stirrer mounted within said fluid reservoir, said stirrer including two members, one of said members being more bendable than the other, detecting a differential bend between said members when said stirrer moves, said differential bend being related to a viscosity of a fluid when the fluid is included in said fluid reservoir.

21. The method of claim 20 wherein detecting said differential bend includes timing the time lapsed between passage of one of said members past a sensor and passage of the other of said members past a sensor, said time lapsed being related to a viscosity of a fluid when the fluid is included in said fluid reservoir.

22. A method of maintaining viscosity placing a fluid in a fluid reservoir, moving a stirrer mounted within said fluid reservoir, said stirrer including first and second members, one of said members being more bendable than the other of said members, detecting a differential bend between said members when said stirrer moves, said differential bend being related to a viscosity of a fluid when the fluid is included in said fluid reservoir, and controlling the addition of a solvent from a solvent reservoir to a fluid within said fluid reservoir.

23. The method of claim 22 wherein detecting said differential bend includes timing the time lapsed between passage of one of said members past a sensor and passage of the other of said members past a sensor, said time lapsed being related to a viscosity of a fluid when the fluid is included in said fluid reservoir.

24. The method of claim 23 wherein the addition of the solvent is automatically controlled and dependent on said time lapsed.

* * * * *